US009464998B2

(12) United States Patent
Zewail et al.

(10) Patent No.: US 9,464,998 B2
(45) Date of Patent: Oct. 11, 2016

(54) METHOD AND SYSTEM FOR ELECTRON MICROSCOPE WITH MULTIPLE CATHODES

(71) Applicant: CALIFORNIA INSTITUTE OF TECHNOLOGY, Pasadena, CA (US)

(72) Inventors: Ahmed H. Zewail, Pasadena, CA (US); John Spencer Baskin, Pasadena, CA (US); Haihua Liu, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/745,122

(22) Filed: Jun. 19, 2015

(65) Prior Publication Data

US 2016/0005566 A1  Jan. 7, 2016

Related U.S. Application Data

(60) Provisional application No. 62/014,823, filed on Jun. 20, 2014.

(51) Int. Cl.
*H01J 37/073* (2006.01)
*G01N 23/205* (2006.01)
*G01N 23/20* (2006.01)
*G01N 23/04* (2006.01)
*H01J 37/20* (2006.01)
*H01J 37/26* (2006.01)
*G01N 21/00* (2006.01)
*H01J 37/22* (2006.01)

(52) U.S. Cl.
CPC ......... *G01N 23/2055* (2013.01); *G01N 21/00* (2013.01); *G01N 23/04* (2013.01); *G01N 23/20058* (2013.01); *G01N 23/20083* (2013.01); *H01J 37/228* (2013.01); *H01J 37/26* (2013.01); *H01J 2237/0635* (2013.01); *H01J 2237/06333* (2013.01); *H01J 2237/2482* (2013.01); *H01J 2237/2617* (2013.01); *H01J 2237/2626* (2013.01)

(58) Field of Classification Search
CPC ...... H01J 37/073; H01J 37/26; H01J 37/295; H01J 2237/06333; G01N 23/04; G01N 23/20058; G01N 23/20083; G01N 23/205; G01N 23/2055
See application file for complete search history.

(56) References Cited

U.S. PATENT DOCUMENTS 7,154,091 B2 * 12/2006 Zewail ................ H01J 37/073 250/307
7,301,263 B2 * 11/2007 Maldonado ......... H01J 37/073 313/103 CM

* cited by examiner

*Primary Examiner* — Jack Berman
(74) *Attorney, Agent, or Firm* — Kilpatrick Townsend & Stockton LLP

(57) ABSTRACT

An electron microscope system includes a laser system operable to generate an optical pulse and a pump pulse and a microscope column. The microscope column includes a multiple cathode structure having a plurality of spatially separated cathode regions. Each of the cathode regions are operable to generate an electron pulse. The microscope column also includes an electron acceleration region adjacent the multiple cathode structure, a specimen region operable to support a specimen, and a detector.

19 Claims, 11 Drawing Sheets

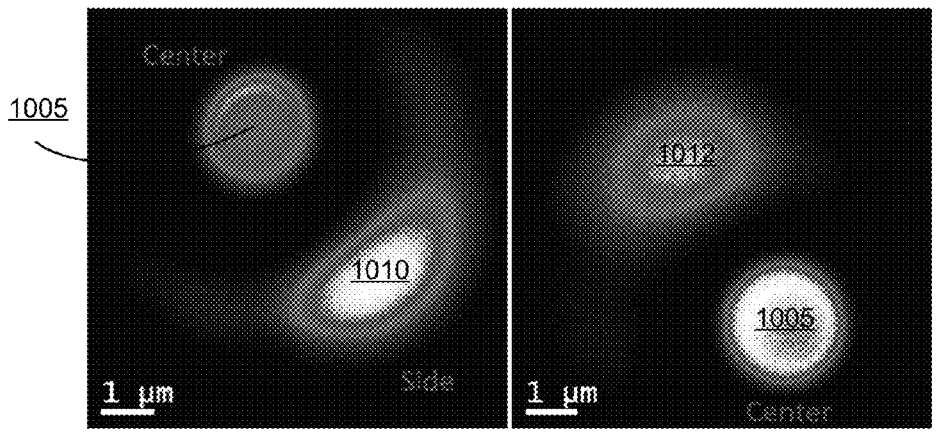
FIG. 10A   FIG. 10B
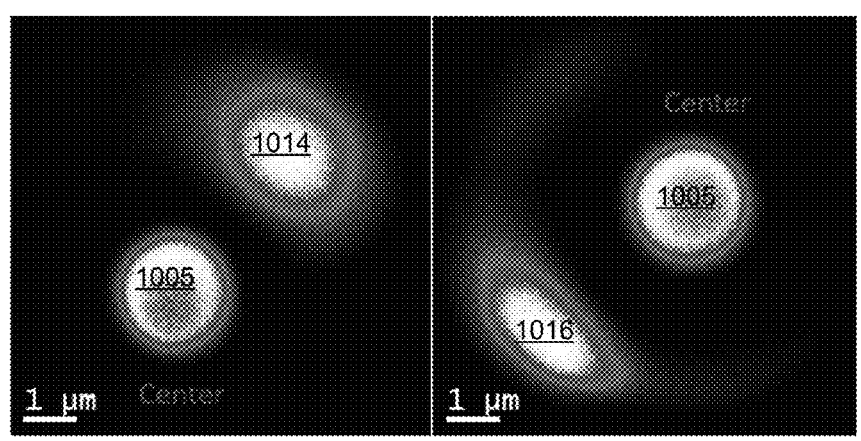
FIG. 10C   FIG. 10D
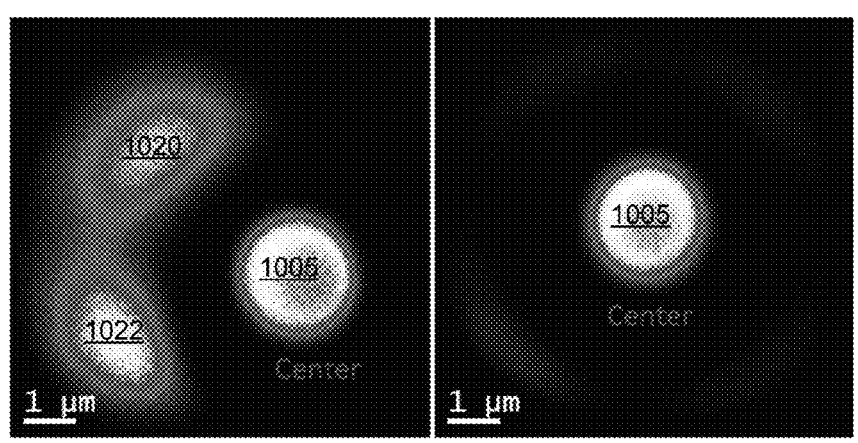
FIG. 10E   FIG. 10F

METHOD AND SYSTEM FOR ELECTRON MICROSCOPE WITH MULTIPLE CATHODES

CROSS-REFERENCES TO RELATED APPLICATIONS

This application claims priority to U.S. Provisional Patent Application No. 62/014,823, filed on Jun. 20, 2014, entitled "4D Multiple-Cathode Electron Microscope," the disclosure of which is hereby incorporated by reference in its entirety for all purposes.

STATEMENT AS TO RIGHTS TO INVENTIONS MADE UNDER FEDERALLY SPONSORED RESEARCH OR DEVELOPMENT

This invention was made with government support under DMR0964886 awarded by the National Science Foundation and under FA9550-11-1-0055 awarded by the Air Force. The government has certain rights in the invention.

BACKGROUND OF THE INVENTION

In 4D ultrafast electron microscopy (UEM), ultrafast light pulses generate electron packets by photoemission at the cathode of an electron microscope. The electron packets are then used to probe dynamic processes initiated by heating or by exciting the microscopic specimen with a second, synchronized ultrafast light pulse. In conventional implementations, each pump pulse on the specimen is accompanied by one suitably delayed laser pulse on the cathode to generate one packet of electrons probing a single time point in the evolution of the specimen. A record of the full course of the temporal evolution of the specimen is then constructed by repeating the experiment multiple times with variation of the delay time between the two light pulses, reading out a separate CCD image for each delay time. Thus, information about different time points in the dynamic response of the specimen is obtained from different excitation events.

Conventional techniques are well suited for specimens that undergo irreversible, but sufficiently well-defined dynamics, to allow a new specimen area to be used for each time point or for a specimen that recovers fully to allow repeated identical excitations of the same area.

Despite the progress made in the field of UEM, there is a need in the art for improved methods and systems related to electron microscopy.

SUMMARY OF THE INVENTION

The present invention relates generally to methods and systems related to microscopy. In a particular embodiment, methods and systems are provided that enable the capture of multiple images at ultrashort time intervals for a single microscopic dynamic process, which can be referred to as 4D multiple-cathode ultrafast electron microscopy (UEM). The techniques described herein are applicable to the study of a wide variety of materials and a range of microscope configurations.

In an embodiment, the dynamic process is initiated in the specimen by one femtosecond light pulse (referred to herein as a pump pulse) and probed by multiple packets of electrons generated by one ultraviolet laser pulse (referred to herein as an optical pulse) impinging on multiple, spatially-distinct, cathode surfaces or elements. Each electron packet is distinctly recorded, with timing and detector location controlled by the cathode configuration. As an example, two packets of electrons on each image frame (of a CCD camera) can probe different times, separated by a time delay on the order of tens of picoseconds, in the evolution of the diffraction of a gold film following femtosecond heating. The electron packets originate from different cathode locations or regions, pass through the same area of the specimen, and are recorded at distinct locations on the detector, thereby encoding two different time points in the evolution of the specimen. Embodiments of the present invention provide methods and systems for imaging of irreversible ultrafast phenomena of materials and studies involving the single-frame capture of ultrafast dynamics using single-pump/multiple-probe, embedded stroboscopic, imaging.

As described more fully herein, the present invention makes it possible to probe and distinctly record multiple time points in a dynamic process following a single initiation pulse. In an embodiment, the probing electron packets are all generated by a single light pulse, which impinges on multiple, spatially-distinct, cathode surfaces. Time separations between electron packets in the electron-pulse train are adjusted by the cathode spatial and electrostatic configuration.

According to an embodiment of the present invention, an electron microscope system is provided. The electron microscope system includes a laser system operable to generate an optical pulse and a pump pulse and a microscope column. The microscope column includes a multiple cathode structure having a plurality of spatially separated cathode regions. Each of the cathode regions are operable to generate an electron pulse. The microscope column also includes an electron acceleration region adjacent the multiple cathode structure, a specimen region operable to support a specimen, and a detector.

According to another embodiment of the present invention, a method of operating an electron microscope is provided. The method includes directing an optical pulse to impinge on a cathode structure having a plurality of cathode regions and generating a plurality of electron pulses, each of the plurality of electron pulses being associated with one of the plurality of cathode regions. The method also includes accelerating the plurality of electron pulses to impinge on a specimen and directing a pump pulse to imping on the specimen. The method further includes detecting a signature associated with the plurality of electron pulses after the plurality of electron pulses have passed through the specimen and processing the signature to provide an output at an output device.

According to a specific embodiment of the present invention, a method of analyzing a specimen using an electron microscope is provided. The method includes directing a first laser pulse to impinge on a cathode structure of the electron microscope, directing a second laser pulse to impinge on the specimen, generating a first electron pulse from a first cathode region of the cathode structure in response to the first laser pulse, and generating a second electron pulse from a second cathode region of the cathode structure in response to the first laser pulse. The method further includes accelerating the first electron pulse and the second electron pulse towards the specimen and directing the first electron pulse and the second electron pulse to impinge on the specimen. The first electron pulse impinges on the specimen at a first time and the second electron pulse impinges on the specimen at a second time after the first time.

The method further includes passing the first electron pulse and the second electron pulse through the specimen, detecting a signature associated with the first electron pulse and the second electron pulse, and providing an output associated with the detected signature.

Numerous benefits are achieved by way of the present invention over conventional techniques. For example, embodiments of the present invention provide techniques that probe the ultrafast dynamics of microscopic specimen at multiple time delays in the femtosecond to picosecond time range following a single excitation pulse. Additionally, some embodiments multiply the data acquisition rate in measurements of ultrafast dynamics, thereby reducing experiment duration and exposure of the specimen to laser pumping. Furthermore, some embodiments enable internal calibration of the single pulse dynamics by the direct recording of a negative-time reference on each data frame and allow adjustment of the probe pulse time delays by electrostatic cathode settings. These and other embodiments of the invention along with many of its advantages and features are described in more detail in conjunction with the text below and attached figures.

BRIEF DESCRIPTION OF THE DRAWINGS

FIG. 10A-10F are images illustrating different multiple electron beam configurations for a multiple cathode electron microscope according to an embodiment of the present invention.

DETAILED DESCRIPTION OF SPECIFIC EMBODIMENTS

In order to study samples with completely non-repetitive dynamics, for example, a stochastic process in a heterogeneous sample that does not return to its initial configuration, a series of snap shots following a single excitation event can provide the only direct and detailed view of the evolution. Currently, single excitation pulse systems combined with video-mode imaging can provide millisecond-scale time resolution, far short of the time scale for many phenomena of interest in nanoscale materials science, chemistry, and physics. Nanosecond resolution has been reached by combining one excitation pulse with a train of light pulses on a single cathode, with deflection of the imaging electrons after passing the specimen plane to direct each successive pulse to a new region of the detector. This nanosecond method has been successfully used with a high-speed electrostatic deflector array to obtain time sequences of irreversible and stochastic processes.

Various implementations of UEM that achieve laser-based time-resolved microscopy have been utilized, including single-pulse UEM, which enables "singe-shot" imaging of homogeneous specimens, stroboscopic UEM, which uses a series of optical pulses impinging on a single cathode, and single-cathode, deflection techniques, which use a series of optical pulses impinging on a single cathode to generate a series of electron pulses that are swept across a detector through image deflection. In contrast with these conventional techniques, embodiments of the present invention utilize the stable geometry of the microscope column and the high level of control over the applied voltages that is achievable to provide a high level of precision in both image timing (on the order of picoseconds) and image location.

Embodiments of the present invention achieve increased timing accuracy with respect to conventional techniques through the use of multiple cathodes. As an example, embodiments of the present invention provide picosecond resolution. Although some embodiments of the present invention are described in relation to diffraction measurements, the present invention is not limited to these particular configurations and image based applications are included within the scope of the present invention.

Figure 1A:
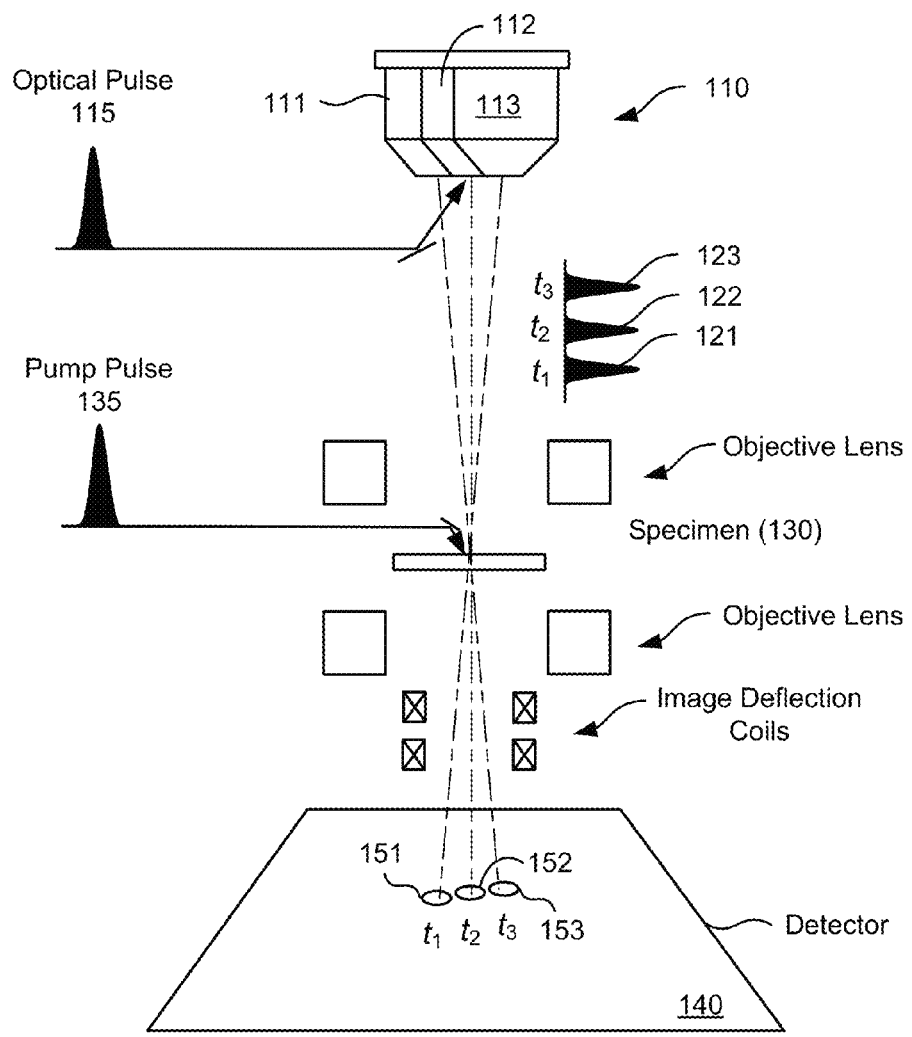
FIG. 1A is a simplified schematic diagram illustrating elements of a multiple cathode electron microscope according to an embodiment of the present invention.

FIG. 1A is a simplified schematic diagram illustrating elements of a multiple cathode electron microscope according to an embodiment of the present invention. As illustrated in FIG. 1A, a cathode structure 110, which can also be referred to as an electron photoemission source, including multiple cathodes (i.e., cathodes 111, 112, and 113) is provided in the microscope column. Laser irradiation represented by single optical pulse 115 is incident on the cathode structure 110. A set of time separated electron pulses 121, 122, and 123 are produced by the cathode structure and are accelerated toward the specimen 130, also referred to as a sample. Objective lenses are positioned adjacent the specimen for imaging purposes.

In some embodiments, the optical pulses 115 used to generate the electron beams from the multiple cathodes are shaped spatially, temporally, or combinations thereof to enhance the electron beams produced by the multiple cathodes. Gaussian beams with top-hat temporal profiles (e.g., 250 fs in length) are utilized in some implementations although this particular beam profile is not required by the present invention. In other embodiments, as an example, the shape of the optical pulse 115 can be provided such that the electron pulses are chirped, which will result in pulse compression as the electron pulse propagates toward the specimen. In addition to electron pulse chirping, other temporal pulse shaping techniques that are applicable to single cathode microscopes can be applied to the multiple cathode structures discussed herein. Beam steering can be used to increase the laser intensity at the center and/or edge of the cathode structure in order to enhance electron beam generation.

The specimen is excited using pump pulse 135, which is incident on the specimen. Timing between the optical pulse 115 and the pump pulse 135 is controlled such that the time of arrival of the pump pulse and the electron pulses is coordinated. Optical access to the cathode structure and the specimen are provided as described more fully in relation to FIG. 2. One of ordinary skill in the art would recognize many variations, modifications, and alternatives.

When a specimen irreversibly changes following the pump laser excitation, an image (real space or diffraction) for a single time point can be acquired using the single pulse method of one pump pulse and one electron pulse, after which the detector frame is read out. For a homogeneous specimen, the experiments may be repeated at different time delays (between the pump pulse and the electron pulse reaching the specimen) and on different specimen locations to achieve the equivalent of a full "single-shot" transient. When, instead, conditions of repeatability are met, acquisition of a single image for a single time delay may also be carried out stroboscopically by using identical pump/probe cycles that are repeated as many times as required to accumulate a single image frame of the desired quality before detector read-out. Additional time points can be acquired at the same specimen location. Both acquisition modes have thus far been used by the present inventors with only a single probe pulse per excitation. The time resolution achieved with the stroboscopic method took microscopy into the femtosecond regime, while in the "single-shot" recording hitherto, the resolution was typically on the nanosecond scale.

Referring to FIG. 1A, a multiple-cathode technique is illustrated that is characterized by the ultrafast time scale (on the order of picoseconds) accessible for imaging. Additionally, high precision in image timing and location on the detector are intrinsic features of the present invention. As illustrated in FIG. 1A, the delivery of one laser pulse to both the specimen (i.e., a pump pulse 135) and the multiple cathode structure (i.e., the optical pulse 115) is accompanied by a train of temporally-spaced electron pulses 121, 122, and 123, with each from a distinct cathode surface of the multiple cathode structure.

The timing of the electron pulses 121, 122, and 123 is controlled by the source locations and electrostatic potential environments, while, in the implementation illustrated in FIG. 1A, the spatial separation of image locations 151, 152, and 153 depends to a significant extent on the lateral spatial separation of the distinct cathode surfaces.

Figure 1B:
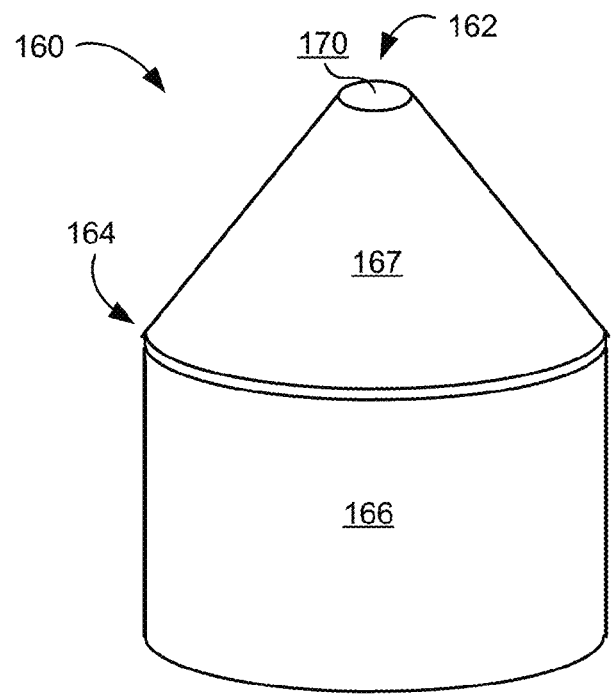
FIG. 1B is a simplified schematic diagram illustrating a cathode structure operable to provide multiple cathodes according to an embodiment of the present invention.

FIG. 1B is a simplified schematic diagram illustrating a cathode structure operable to provide or function as multiple cathodes according to an embodiment of the present invention. As illustrated in FIG. 1B, the cathode structure 160 provides multiple cathode regions, also referred to as cathode elements, for example, two regions: the top 162 of the cathode structure and the side 164 of the cathode structure. The cathode regions are separated in both lateral and longitudinal directions.

Referring to FIG. 1B, the cathode structure 160 includes a cylindrical region 166 (which defines a longitudinal direction) and a tapered section 167 that begins at the side 164 of the cathode structure, which can also be referred to as a side region, and ends at the top 162 of the cathode structure, which can also be referred to as a tip region. Thus, the cathode structure 160 includes a tip region 162 and a side region 164. As described more fully below, the side region 164 is only one of several side regions that are present on the cathode structure. A single side region is illustrated for purposes of clarity.

Figure 6:
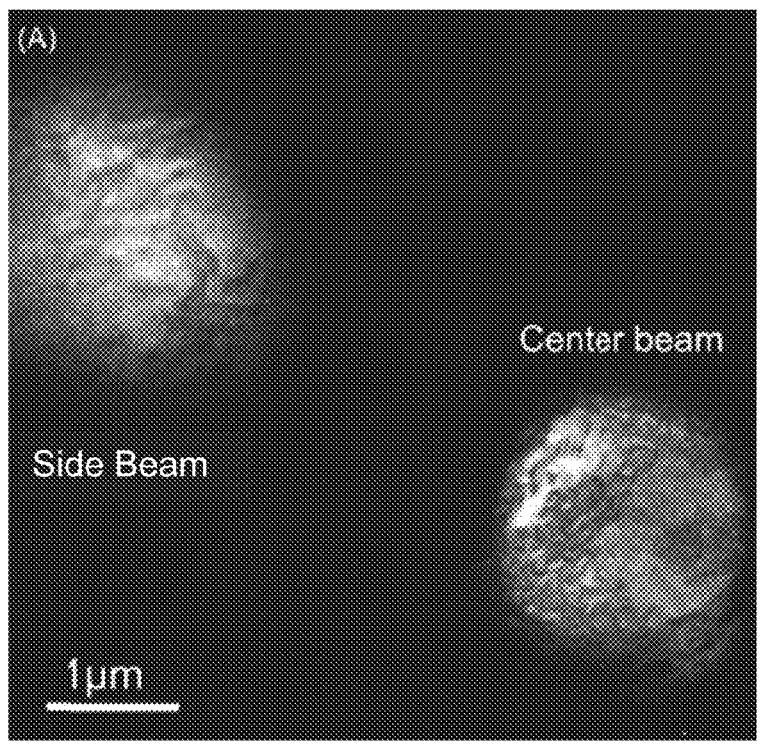
FIG. 6 is an image of a gold film illuminated with two pulsed electron beams according to an embodiment of the present invention.

In response to optical illumination, the tip region 162 generates a center beam of electrons, which can be associated with the tip region of the cathode structure. Referring to FIG. 6, the center beam is illustrated in the lower right corner of the image. The cathode structure 160 also includes a tapered section 167 that spatially separates the tip region 162 from the side region 164 in both a lateral dimension and a longitudinal dimension aligned with the center axis of the cylindrical region 166. The side region is defined by the intersection at which the cylindrical portion of the cathode rod meets the cone shaped region of the cathode. The side region 164 generates a side beam of electrons, illustrated as the side beam in the top left corner of the image in FIG. 6.

In other embodiments, multiple cathode regions that are spatially separated in the lateral dimension but substantially coplanar in the longitudinal direction are utilized. In some implementations, the flat area 170 at the highest point of the tip region 162 is about 50 μm in diameter. Of course, other sizes can be used depending on the particular application.

In some embodiments, the cylindrical region 166 is replaced with a rod that is characterized by a quadrilateral (e.g., rectangular or square) cross section. In these embodiments, the side region will be formed at either the intersection of the tapered region and the sides of the quadrilateral or at the intersection of the tapered region and the corners of the quadrilateral. One of ordinary skill in the art would recognize many variations, modifications, and alternatives.

Figure 1C:
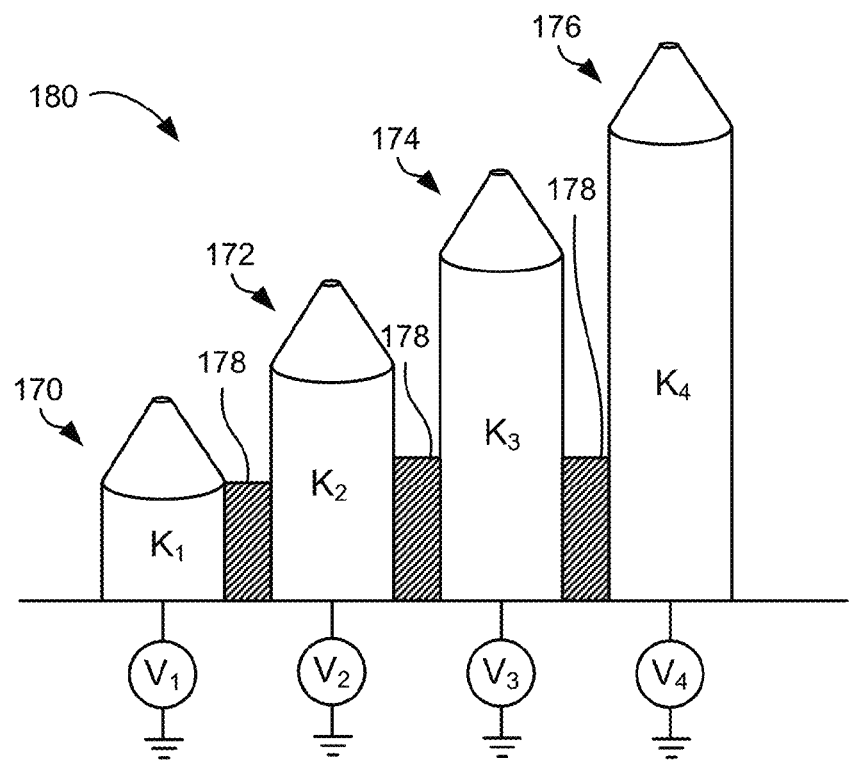
FIG. 1C is a simplified schematic diagram illustrating a multi-voltage multi-cathode structure according to an embodiment of the present invention.

FIG. 1C is a simplified schematic diagram illustrating a multi-voltage multi-cathode structure according to an embodiment of the present invention. In the structure illustrated in FIG. 1C, the cathode structure 180 includes a plurality of separate cathode elements 170, 172, 174, and 176, which provide separate emitting surfaces. Although four cathode elements are illustrated, the present invention is not limited to this number and other numbers of cathode elements can be utilized according to an embodiment of the present invention. Although the cathode elements are illustrated as conical in shape and arranged in a linear configuration this is not required by the present invention and other shapes including flat, angled, or pyramidal, and other configurations such as a hexagonal array with the central cathode element positioned above the peripheral cathode elements in a spiral configuration in which the cathode elements decrease in height from the center towards the periphery, and the like are included within the scope of the present invention. One of ordinary skill in the art would recognize many variations, modifications, and alternatives.

Each of the cathode elements 170, 172, 174, and 176 are separated by an insulator 178 and can be operated at distinct and different voltages, V1, V2, V3, and V4. As an example, the voltage could be varied linearly between the cathode elements or set in an arbitrary manner. In some embodiments, the voltage sources V1, V2, V3, and V4 can be set to a single value to operate at a uniform voltage. The differing voltages applied to each cathode element enable, ultrafast multiple-probe imaging that can be performed with spatial separation of the images on the detector by means of electron energy dispersion in the magnetic sector. Because of the separate voltages for each of the cathode elements, the height of the cathode elements can be different as illustrated in FIG. 1C or the same, since the voltage control enables control over the pulse timing.

As demonstrated herein, the cathode structure provides for spatial separation between the multiple regions emitting the electron beams. In some implementations, the source spatial configuration results in displacement on the detector of the dual images of a given specimen location equal to about half of the displacement, measured in pixels, of corresponding diffraction peaks. Accordingly, to expand the capabilities related to high resolution imaging, a larger separation of source points can be used to increase the image separation, but additionally, establishing a voltage differential between cathodes regions can be utilized. As an example, by incorporating voltage dividing resistances within the design of the multi-surface cathode, different voltages can be applied to each cathode element. Other designs such as that illustrated in FIG. 1C can also be utilized. The electron packets of slightly different energy will then be focused to different spots on the detector as a consequence of the energy dispersion of the magnetic sector. The energy differences designed to space the train of images across the detector will also likely affect the electron packet's timing because of their different drift speeds. For example, a change in electron energy of 1000 V results in a change in the ~4 ns flight time from cathode to specimen of only 6 ps in a 200 keV microscope.

Figure 2:
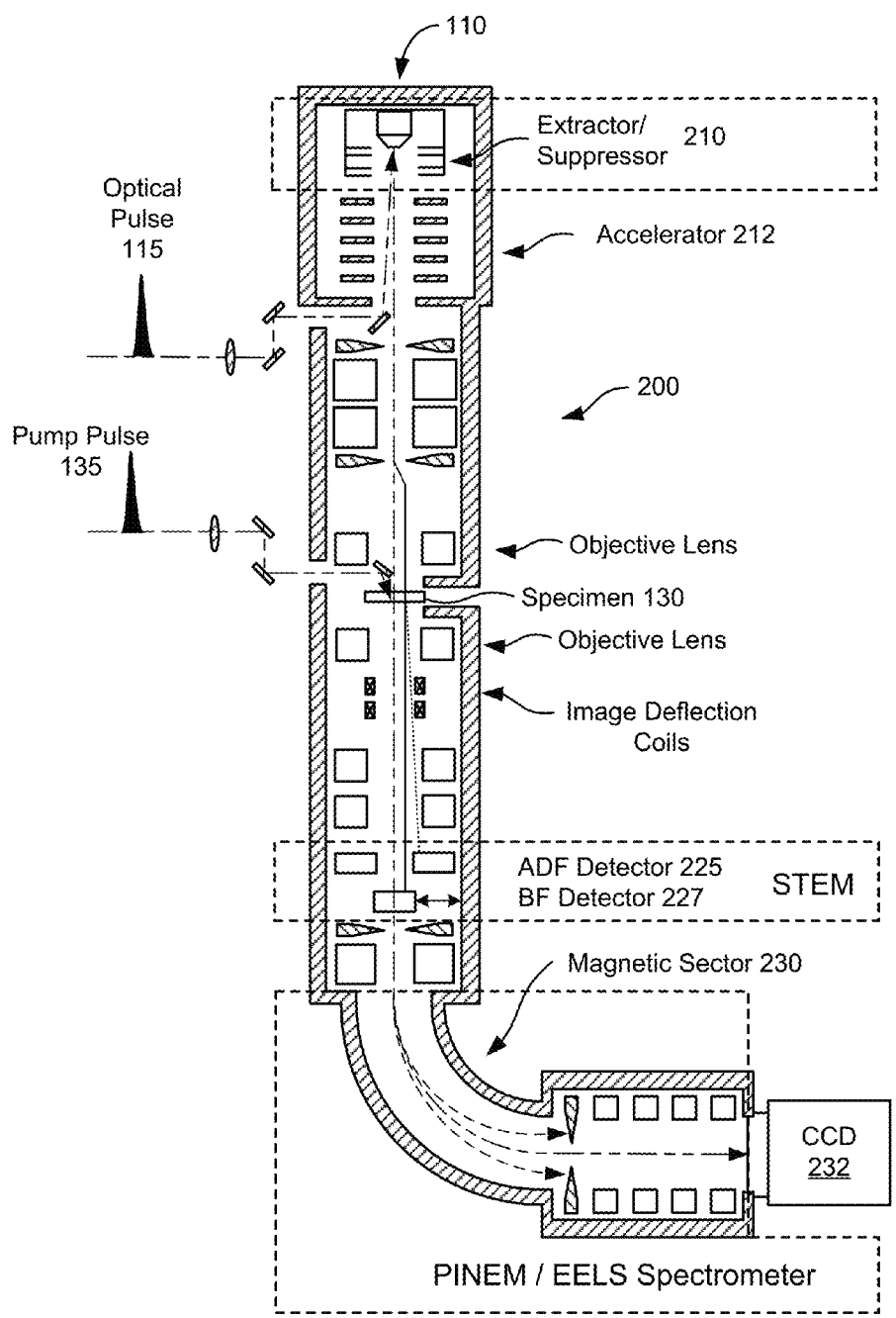
FIG. 2 is a simplified schematic diagram illustrating an electron microscope column utilizing multiple cathodes according to an embodiment of the present invention.

FIG. 2 is a simplified schematic diagram illustrating an electron microscope column utilizing multiple cathodes according to an embodiment of the present invention. In the embodiment of the present invention illustrated in FIG. 2, the 4D microscope (i.e., a 4D UEM) integrates multiple-cathode probe generation in addition to energy filtering as described more fully below. Synchronized femtosecond laser pulses, i.e., optical pulse 115 and pump pulse 135, enter the microscope column through one or more entrance windows, which can be fabricated from materials with high transparency at the laser wavelength and sufficient thickness to provide mechanical rigidity. For example, fused silica windows about 6 mm thick without coatings are used in various embodiments. The optical pulse 115 and the pump pulse 135 are focused on the cathode structure 110 and on the specimen 130, respectively, for UEM operation.

Referring to FIG. 2, the 200 keV microscope column 200 is illustrated and is configured to admit separate laser irradiation of the specimen 130 and of the cathode structure 110 (i.e., a field emission gun configuration) that includes multiple cathode regions. After emission from the cathode structure 110, the multiple electron beams are accelerated through an extractor/suppressor region 210 and then through an accelerator 212 to accelerate the electron beams down the column toward the specimen.

The microscope includes an annular dark field (ADF) detector 225 and a bright field (BF) detector 227 to provide for scanning transmission electron microscope (STEM) operation. In order to provide for energy filtering, the magnetic sector 230 is used to direct the electron beams through a 90° turn to reach the CCD camera 232, providing the capability of electron energy loss spectroscopy (EELS) or photon-induced near-field electron microscopy (PINEM). Additional description related to EELS is provided in U.S. Pat. No. 8,203,120 and additional description related to PINEM is provided in U.S. Pat. No. 8,429,761, the disclosures of which are hereby incorporated by reference in their entirety for all purposes. According to embodiments of the present invention, a unique optical arrangement is utilized to provide for precision-control of the excitation pulse on the specimen. The optical pulse 115 (e.g., a femtosecond ultraviolet (UV) pulse) and the pump pulse 135 (e.g., a green laser pulse) that are directed to the cathode structure and the specimen, respectively, can be generated using a single infrared laser source operating at a user-selectable repetition rate. In other embodiments, multiple laser sources are utilized. As will be evident to one of skill in the art, embodiments of the present invention are not limited to these particular wavelengths of light and other wavelengths can be utilized according to other embodiments. The pump pulse beam passes through a variable optical delay path (not shown) to adjust the relative timing of the pulses before their arrival at the microscope. In some implementations, the electron pulses are recorded using a 2048×2048 pixel CCD 232.

The timing differential should be strongly dependent on the earliest stage of electron acceleration at each surface and may be adjustable to a significant extent by variation of the applied extraction fields, allowing additional control of experimental conditions. Given the longitudinal spatial separation of micrometers to millimeters that could be designed, we see the potential to generate multiple, ultrafast electron packets separated by femtosecond to picosecond delays in single-frame imaging, subject only to pulse-width limitations.

Figure 3:
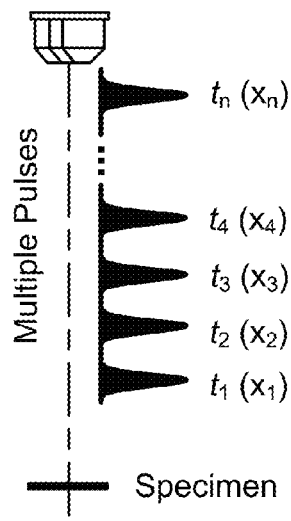
FIG. 3 is a diagram illustrating multiple electron pulses emitted from multiple cathodes of an electron microscope according to an embodiment of the present invention.

FIG. 3 is a diagram illustrating multiple electron pulses emitted from multiple cathodes of an electron microscope according to an embodiment of the present invention. In the implementation illustrated in FIG. 3, a train of electron packets or pulses with different arrival times $t_i$ is generated by a single optical (e.g., a UV laser pulse) incident at multiple, spatially separate cathode positions ($x_i$). The multiple-cathode operation illustrated in FIG. 3 results in the generation of n electron pulses at times $t_1$ to $t_n$, each of the electron pulses being associated with a separate cathode location represented by coordinates $x_1$ to $x_n$. Each electron packet follows its own path down the microscope column to the specimen area under investigation, and is afterward detected at a separate area on the CCD. Although shown as a single optical path in FIG. 3, it will be evident to one of skill in the art that the electron pulses follow separate paths as a result of the different cathode regions and can pass through the specimen at substantially the same location. Thus, both spatial and temporal separation of each of the electron pulses in the detector plane is provided by embodiments of the present invention. It should be noted that in FIG. 3, the n electron packets are illustrated as equally separated in time, but this is not required by the present invention and the time delay between pulses could be non-uniform. One of ordinary skill in the art would recognize many variations, modifications, and alternatives.

Figure 4:
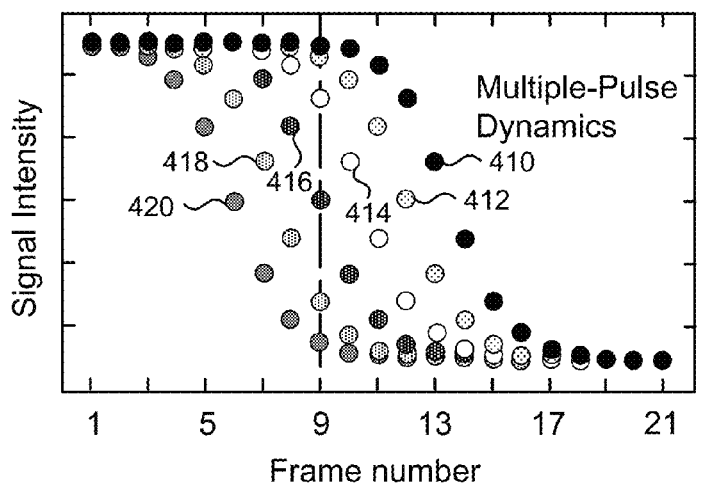
FIG. 4 is a plot illustrating measurement of electron packets as a function of optical delay according to an embodiment of the present invention.

FIG. 4 is a plot illustrating measurement of electron packets as a function of optical delay achieved by changing the pump pulse optical path length according to an embodiment of the present invention. As illustrated in FIG. 4, which plots the measured intensity at the detector as a function of frame number, the multiple-cathode UEM measurement of the specimen displays a drop in signal intensity (e.g., diffraction or image configuration) following laser excitation by the pump pulse. In FIG. 4, six electron packets equally separated in time probe the specimen for each excitation and are recorded in a single image frame numbered 1 through 21.

The signals from each packet are plotted for a series of frames recorded for changing time delay between the specimen and cathode excitation laser pulses. In other words, the signals from each of the six electron packets in a given frame are plotted at the x coordinate corresponding to that frame. A series of frames are recorded for increasing time delay between the laser pulses for the specimen and the cathode structure irradiation. Signals from the first through the last packets to reach the specimen are represented by circles 410, 412, 414, 416, 418, and 420, respectively. It should be noted that measurements associated with the last packets 420 exhibit a decrease in intensity at earlier frames because these packets arrive at the specimen after the pump pulse interacts with the specimen and changes in the specimen are evident in the early frames for these late packets. In contrast, the first packets 410 arrive at the specimen (i.e., frames 1-9) before arrival of the pump pulse, resulting in high intensity values. Thus, as shown in FIG. 4, for the first electron pulse or packet 410, the pump pulse reached the specimen at approximately frame 9 or 10. For the last electron pulse or packet 420, the pump pulse reached the specimen at approximately frame 1 or 2.

Considering the multiple pulse dynamics illustrated in FIG. 4, it is possible to provide an in-frame reference using embodiments of the present invention. In measurement situations for which changes occur during measurement, an in-frame reference can be established by having the pump pulse arrive at the specimen between two electron pulses. The first electron pulse will provide information on the specimen before the pump pulse arrives and the second electron pulse will provide information on the specimen after the pulse arrives at the specimen. Thus, the first electron pulse provides a reference for the material being studied. In conventional approaches using samples that are changing, it can be difficult to determine if changes are resulting from changes initiated by the pump pulse or other changes in the system. The reference pulse provides a method to optimize and modify the microscope operating parameters and/or the specimen with the confidence that changes in measurements are due to a single pump pulse interaction with the specimen.

Thus, embodiments of the present invention provide a measurement system in which the pump pulse can be placed in time between the time that the first electron pulse (e.g., the center pulse) and the second electron pulse (e.g., the side pulse) arrive at the specimen. The second electron pulse can then be delayed, for example, from 20 ps to 30 ps to 40 ps while maintaining the first electron pulse at the initial spatial position and time of arrival.

Figure 5:
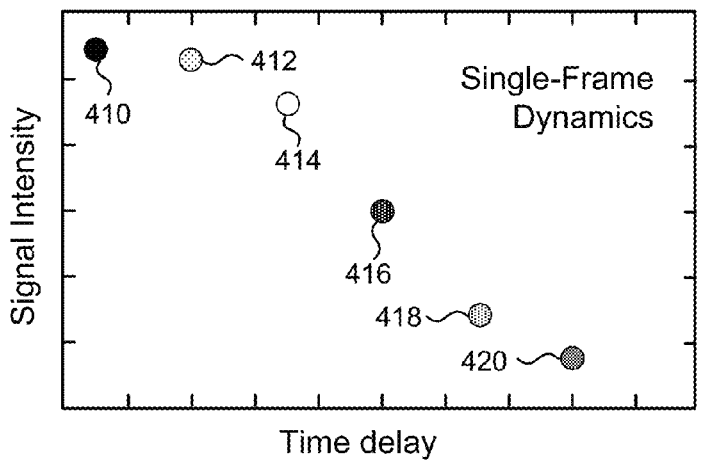
FIG. 5 is a plot illustrating temporal behavior of electron packets in a single frame according to an embodiment of the present invention.

FIG. 5 is a plot illustrating temporal behavior of electron packets in a single frame according to an embodiment of the present invention. In FIG. 5, the data from the six electron packets of a single frame (i.e., frame 9) from FIG. 4 are plotted on a time axis that accounts for the relative timing of the packets (i.e., the time delays between the packets). This analysis provides a temporal record of essentially the full transition dynamics of the specimen for the particular frame of interest. In order to determine the time delay illustrated in FIG. 5, the time associated with zero delay for each individual electron pulse is determined. This zero delay time can be determined by measuring a correlation between the pump laser pulse and the electron pulse.

FIG. 6 is an image of a gold film illuminated with two pulsed electron beams according to an embodiment of the present invention. To collect this data, an 11 nm thick oriented gold crystal film on a copper grid was excited by femtosecond pulses of 519 nm light at a fluence of 1.6 mJ/cm$^2$. As a result of the excitation of the cathode structure, two electron beams were generated. In this implementation, a conical lanthanum hexaboride ($LaB_6$) cathode (90° cone-angle) was utilized as the cathode structure. The first electron beam was generated from the top of the cathode structure (i.e., the center flat of the cathode) and the second electron beam was generated from a side of the cathode structure (i.e., a projecting edge of the conical taper of the cathode). The distribution of electron counts between the two electron packets or beams was balanced by control of the alignment of the optical pulse (i.e., the UV beam) and the field emission gun tilt. The electron beams were incident on the specimen along the gold [100] zone axis.

As illustrated in FIG. 6, the illumination of the gold film by the two pulsed electron beams generated by photoemission at the two locations on the cathode structure produced approximately 2 μm image spots at the detector plane that are separated by several microns. The spatial separation between the image spots correlates with the physical separation between the cathode regions from which the electron beams were generated. In FIG. 6, the labels "center" and "side" refer to the source location on the top and side of the cathode structure, respectively. Additionally, although not illustrated in FIG. 6, the center beam and the side beam are delayed in time (e.g., by a few tens of picoseconds) with respect to each other.

According to an embodiment of the present invention, an imaging experiment can be performed using a uniform sample. The different beams produced by the different cathode regions can be focused onto different portions of the uniform or homogeneous specimen. As the two or more beams, which are staggered in time, pass through different portions of the uniform specimen, the dynamics induced by the pump pulse in the two different portions can be analyzed. Thus, using embodiments of the present invention, two different locations on the sample can be measured sequentially using electron beams impacting the sample at different times. This technique is of particular value in measuring non-reversible transitions as a function of time.

Figure 7:
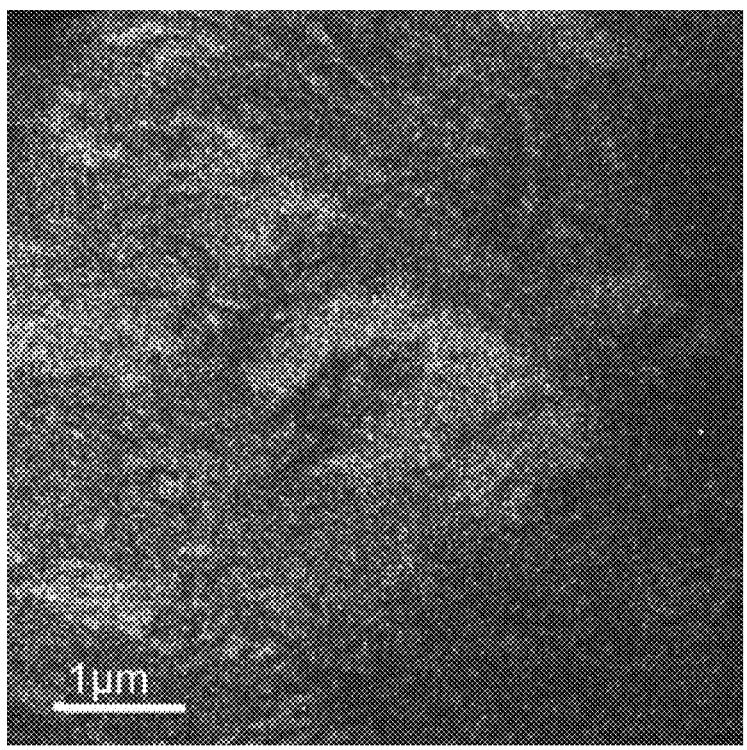
FIG. 7 is an image of the gold film illustrated in FIG. 6 during uniform intensity illumination using two pulsed electron beams according to an embodiment of the present invention.

FIG. 7 is an image of the gold film illustrated in FIG. 6 during uniform intensity illumination using two pulsed electron beams according to an embodiment of the present invention. In FIG. 7, the beams illustrated in FIG. 6 are shown after spreading of their intensity to overlap and to uniformly cover the area of study on the specimen (i.e., the center of the image). Thus, FIG. 7 illustrates the center beam and the side beam as coincident at the specimen.

In some embodiments, during collection of data, a selected-area aperture was used to select only the central region shown in FIG. 7 that was illuminated uniformly by each of the two electron beams. Thus, by spreading the multiple beams over an area larger than that passed by an aperture in the system, the two beams, although not completely overlapping, can measure a single region of the specimen. The diffraction pattern obtained from this specimen region under these conditions is shown in FIG. 8.

As illustrated by FIGS. 6 and 7, embodiments of the present invention provide several different measurement conditions, including two electron beams (i.e., probe beams) staggered in time passing through a single location on the specimen or through different locations on the specimen. In other words, the electron beam diameters can be small enough so that the beams are separated when they impinge on the specimen as illustrated in FIG. 6 or the beam diameter can be increased such that the beams overlap each other at the specimen as illustrated in FIG. 7.

Figure 8:
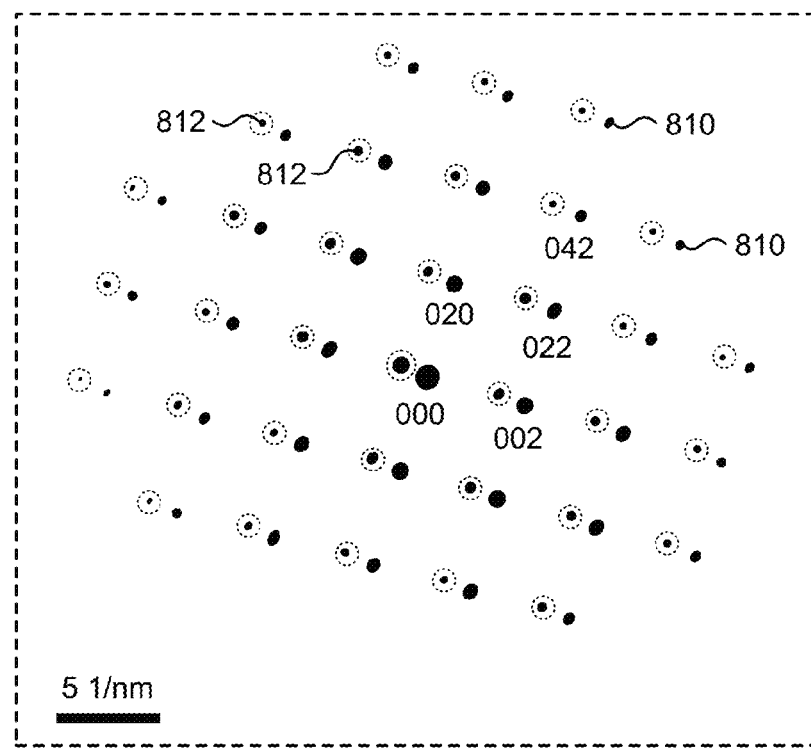
FIG. 8 is a diffraction pattern from a gold crystal film during uniform intensity illumination using two pulsed electron beams according to an embodiment of the present invention.

FIG. 8 is a diffraction pattern from a gold crystal film during uniform intensity illumination using two pulsed electron beams according to an embodiment of the present invention. Thus, in this figure, the conditions illustrated in FIG. 7 were utilized to measure the diffraction patterns shown for the oriented gold crystal film from the two pulsed electron beams. The illustrated diffraction pattern can be referred to as a signature associated with the plurality of electron pulses after they pass through the specimen. Although diffraction from the gold crystal film is illustrated in FIG. 8, embodiments of the present invention are not limited to measurement of diffraction patterns and imaging, PINEM, EELS, and other microscopy techniques are included within embodiments of the present invention.

As illustrated in FIG. 8, a set of distinct peaks was formed for each of the two electron beams produced by the multiple cathode structure. For this particular alignment regime, the side beam, identified by the diffraction peaks 810 not surrounded by circles, was the more intense of the two. The diffraction peaks 812, surrounded by circles to aid in identification, are the peaks that were associated with the center beam generated from the top of the cathode structure.

Figure 9:
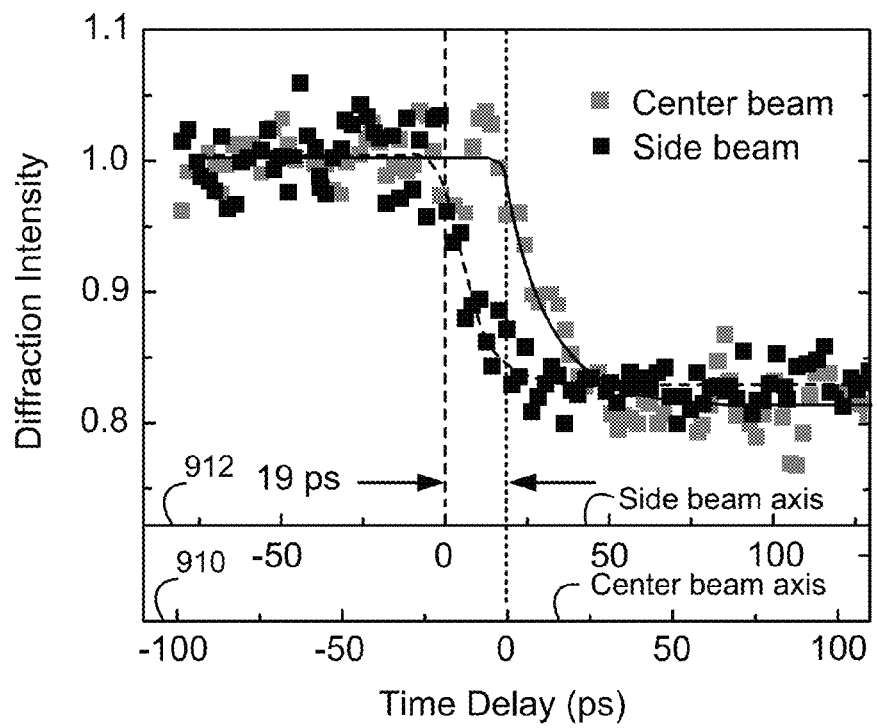
FIG. 9 is a plot of diffraction intensity as a function of time for two pulsed electron beams originating from two cathodes according to an embodiment of the present invention.

FIG. 9 is a plot of diffraction intensity as a function of time for two pulsed electron beams originating from two cathodes according to an embodiment of the present invention. The diffraction intensity illustrated in FIG. 9 is a sum of the diffraction peaks (e.g., the eight peaks) for a given beam as illustrated in FIG. 8. This plot illustrates the dynamics of the diffraction intensity recorded by scanning the laser time delay. Data from the two electron packets are plotted in grey for the center beam and black for the side beam, probing two time delays in each frame. The lower intensity center beam data was filtered to remove high frequency noise. Fits of the time evolution of each transient yield the indicated time separation of 19 ps.

The diffraction intensity as a function of time was measured by scanning over the relative delay of the excitation pulse impinging on the cathode structure (i.e., optical pulse) and the pump laser pulse. For each recorded frame, the average integrated intensity was evaluated for the eight {042} peaks in the diffraction pattern associated with each of the beams. Referring to FIG. 8, the peaks (000), (002), (020), and (042) for both beams are illustrated. The values obtained for the center and side beam peaks in a given frame were normalized by their respective (000) intensities and scaled to set the average value from the first 25 frames to one. In FIG. 9, the center and side beam data from a given frame are plotted on the same vertical line, i.e., following the same format as FIG. 4. Here, however, two time axes have been added, and these are described below.

The diffraction intensities of both electron beams show an abrupt drop in moving from left to right in the figure, i.e., as the delay associated with optical pulse 115 increases. The form of this change for both beams matches well with that revealed in previous similar experiments on gold in which heating of the gold sample results in a decrease in diffraction intensity. Without limiting embodiments of the present invention, the inventors believe that the thermal heating of the specimen by the pump pulse results in reduction in the diffraction intensity that results in the drop in signal value following the arrival of the pump pulse at the specimen.

It should be noted that the change in side beam intensity clearly occurs earlier in the sequence of frames than that of the center beam. The signal evolution for each beam has been fit with a single exponential drop to a lower metastable value on the time scale of the plot, and the fit curves are shown as solid lines passing through the sets of center beam and side beam data. The onset of the change in these fits has been used to fix the zero points on the two time axes and to determine that the time separation of the two electron packets is 19 ps. With this knowledge, the axis 910 and the axis 912 have been added and these indicate, for any given frame, the arrival time at the specimen of the center packet and the side packet, respectively, relative to the excitation pulse. Note that the packet originating from the side cathode arrives later in time, as can be seen from the fact that, for any frame between the zero points of the red and green time axes, only the side beam observes a specimen that has already been excited (positive time).

Embodiments of the present invention utilize a multiple-cathode configuration that provides for the generation of a sequence of ultrafast electron pulses (i.e., probe pulses), which can unambiguously track a specimen's response to a given excitation pulse (i.e., an optical pump pulse). Embodiments of the present invention differ in fundamental ways from that of a single cathode with electron packet deflection. Because the electron packets in the single cathode method are not generated with a spatial separation, they must be deflected after the specimen to separate areas of the detector whenever the packet interval is shorter than the camera readout time. In contrast, the multiple cathode technique described herein provides electron beams that originate at separate locations, enabling for both spatial and temporal separation between the electron beams.

Thus, the multiple-cathode system described herein can provide much shorter probe packet intervals than single cathode approaches with extremely stable timing and image spatial separation without major modifications to the standard microscope column configuration. The timing and image location in the conducted experiments are fixed by the cathode spatial configuration, with the packet that travels a longer distance arriving later. Although a conventional cathode provides separate regions suitable to generate multiple electron beams, other cathode structure designs are included within the scope of the present invention, including a cathode structure with a set of spatially displaced emitting surfaces that provides a train of electron packets that will each arrive at the specimen at a different time and will be spatially separated at the detector.

By utilizing embodiments of the present invention, the use of multiple electron probe packets is useful in relaxing the requirement of reversible dynamics. This results, for example, in the case of a gold film, because like most samples, gold tends to be modified more or less quickly by repetitive excitation. Such progressive permanent changes can easily compromise the interpretation of data acquired in the conventional sequential manner. In contrast, multi-cathode systems that provide multi-probe techniques, ensure that the signal measured at each of the time points contained within a single frame correspond to exactly the same specimen condition, and are therefore internally consistent, without a requirement for long term reversibility. Thus, multiple-cathode operation can be profitably embedded with stroboscopic measurement, and clearly provides a manyfold increase in the efficiency of all UEM measurements, while extending UEM applications into the currently inaccessible realm of materials undergoing rapid modifications.

As described herein, electron packets generated at spatially distinct cathode locations can be used to probe distinct time points in a dynamic process initiated by a single femtosecond specimen initiation pulse in UEM. The static nature of the electrostatic environment ensures stable image location and ultrafast timing precision. Using embodiments of the present invention, it is possible to obtain "all-at-once" imaging, with ultrashort time separations, in a single frame at a specific specimen location. Cathodes with multiple emitting regions or surfaces enable spatial separation between electron beams, allowing rapid capture of ultrafast dynamics in all types of specimen, from those undergoing reversible dynamics, to materials under conditions where laser damage is possible, to stochastic processes in single-shot (picosecond or femtosecond) studies. Thus, embodiments of the present invention can be combined with electron energy loss spectroscopy (EELS) and photon-induced near-field electron microscopy (PINEM) as illustrated in FIG. 2.

FIGS. 10A-10F are images illustrating different multiple electron beam configurations for a multiple cathode electron microscope according to an embodiment of the present invention. As illustrated in FIGS. 10A-10F, a four-fold symmetry is present. Without limiting embodiments of the present invention, the inventors believe that the four-fold symmetry arises from the interaction between the optical input beam and the crystal planes of the cathode structure.

Referring to FIGS. 10A-10F, a center beam 1005 and side beams are illustrated. in FIG. 10A, the center beam 1005 and a side beam 1010 positioned in the lower right quadrant is illustrated. By varying the position of the optical beam on the cathode structure, the acceleration voltages for example, the suppressor voltage, the extractor voltage, and/or the gun lens voltage, and other parameters of the microscope column, the electron pulse intensity can be controlled to distribute most of the power in the illustrated center beam 1005 and a side beam 1010 in the lower right quadrant.

In addition to the lower right quadrant, the side beam can be moved with respect to the center beam 1005 such that the side beam is present in other quadrants, including a side beam 1012 in the upper left quadrant as illustrated in FIG. 10B, a side beam 1014 in the upper right quadrant as illustrated in FIG. 10C, and a side beam 1016 in the lower left quadrant as illustrated in FIG. 10D.

FIG. 10E illustrates a condition in which three electron beams are generated from three cathode regions, producing a center beam 1005, a side beam 1020 in the upper left quadrant, and a side beam 1022 in the lower left quadrant. Thus, using the conical cathode structure illustrated in FIG. 1B, three or more different cathode source locations can be achieved. FIG. 10F illustrates a condition in which substantially all electron beam intensity is contained in a single center beam, demonstrating the flexibility provided by embodiments of the present invention.

Thus, as illustrated in FIGS. 10A-10F, the intensity of the center beam of electron pulses and the side beam of electron pulses can be varied, for example, with most of the electron beam intensity being in the center beam (FIG. 10F), generally balanced electron beam intensity in the center beam and the side beam (FIGS. 10A-10D), or electron beam intensity in both the center beam and multiple side beams (FIG. 10E).

Embodiments of the present invention provide both multiple cathode and single cathode operation in a single integrated package. By adjustment of the laser pulse that excites the cathode and the acceleration voltages and other microscope parameters, either multiple cathode or single cathode operation can be achieved. In some multiple cathode implementations, one or more of the multiple cathodes can be selected for use, providing cathodes with different geometries, materials, and the like. One of ordinary skill in the art would recognize many variations, modifications, and alternatives.

With respect to the time of flight of the electron beams generated by the multiple cathodes, the propagation time from the cathode to the specimen and subsequently the detector is a function of the time delay between the incident laser pulse impinging on the different cathode regions and the voltage applied to the electron beams as they are shaped and accelerated down the microscope column.

Although the spatial separation between the multiple cathodes has some impact on electron pulse timing due to the differing arrival time of the laser pulse at the cathode regions, the acceleration process for the electron beams contributes most significantly to the electron pulse timing. Thus, in addition to the shape and dimension of the cathode structure, the timing between the multiple electron pulses is dependent on the fields that are applied to accelerate the individual electron pulses that originate at different regions of the cathode structure. As the electrons experience different fields during acceleration, the electron pulses, which are initially at low energy, propagate at a relatively low velocity toward the extractor. As described below, control of the gun lens voltage and the suppressor voltage provide time delays between electron pulses on the order of tens of picoseconds. Because the acceleration voltages make a significant impact on the electron pulse timing, the timing is adjustable over a significant range through control of the acceleration voltages.

Figure 11A:
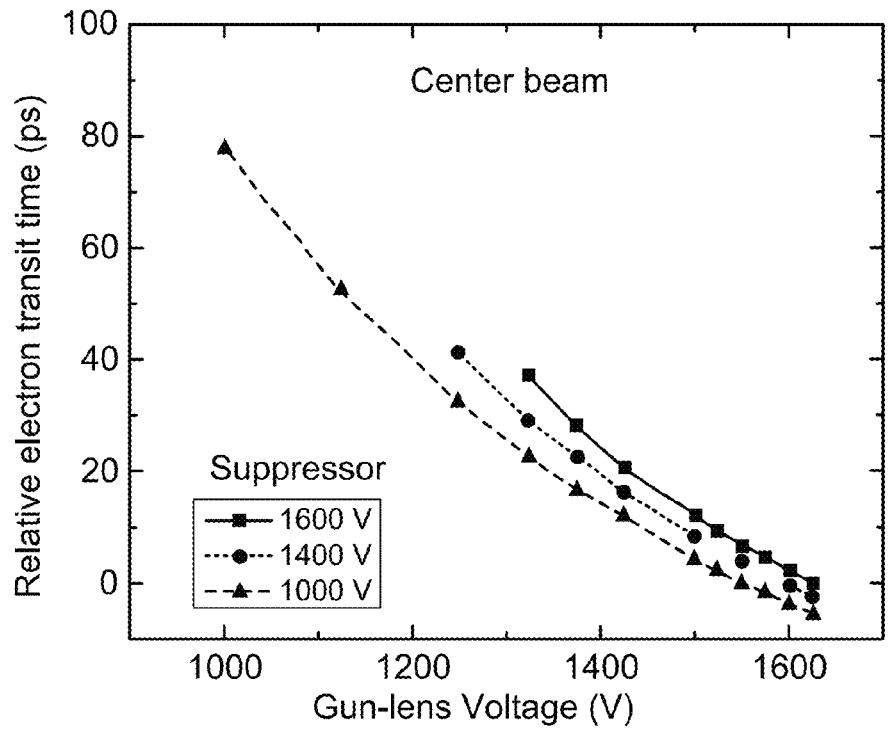
FIG. 11A is a plot illustrating relative electron transit time as a function of gun lens voltage for an electron beam from a center cathode according to an embodiment of the present invention.

FIG. 11A is a plot illustrating relative electron transit time as a function of gun lens voltage for an electron beam from a center cathode according to an embodiment of the present invention. As illustrated in FIG. 11A, for the center beam, control of the gun lens voltage, over a range from 1000 V to ~1600 V, resulted in changes in the relative electron transit time of ~80 ps. As the gun lens voltage is increased, the relative electron transit time decreased in a generally linear manner, providing a high level of control over the electron transit time. Additionally, variation of the suppressor voltage, at levels of 1000 V, 1400 V, and 1600 V, resulted in increases in the relative electron transit time, providing additional control.

Figure 11B:
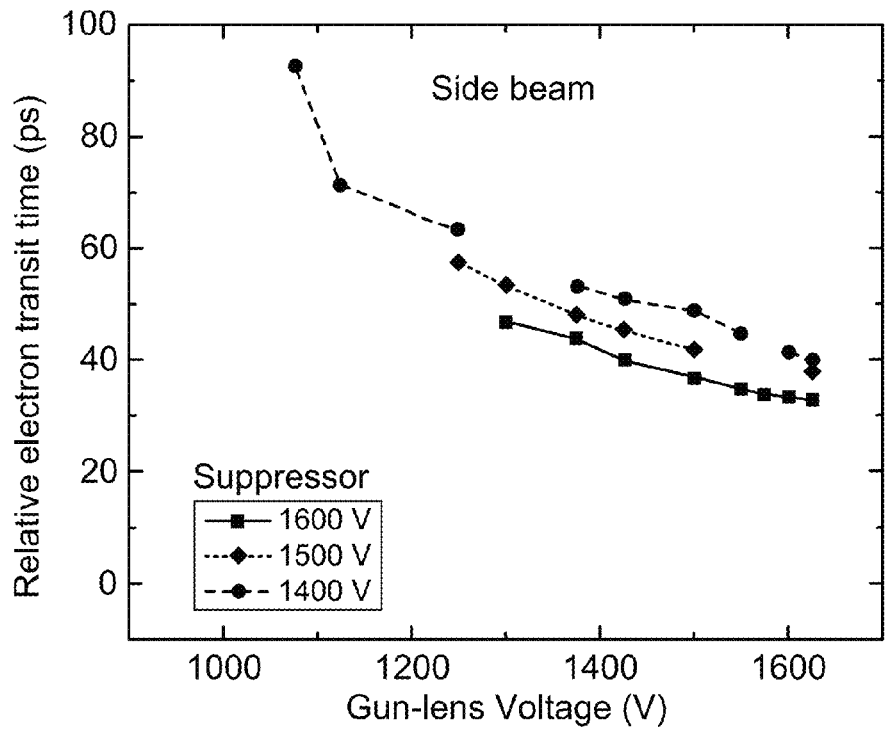
FIG. 11B is a plot illustrating relative electron transit time as a function of gun lens voltage for an electron beam from a side cathode according to an embodiment of the present invention.

FIG. 11B is a plot illustrating relative electron transit time as a function of gun lens voltage for an electron beam from a side cathode according to an embodiment of the present invention. Similar to control of the center beam, the relative electron transit time for the side beam can be controlled over a range of about 60 ps by varying the gun lens voltage from ~1100 V to ~1600 V. As the gun lens voltage is increased, the relative electron transit time decreases. Additionally, control of the suppressor voltage provides an additional, although smaller, level of control of the relative electron transit time, with increases in suppressor voltage decreasing the relative electron transit time.

Figure 12A:
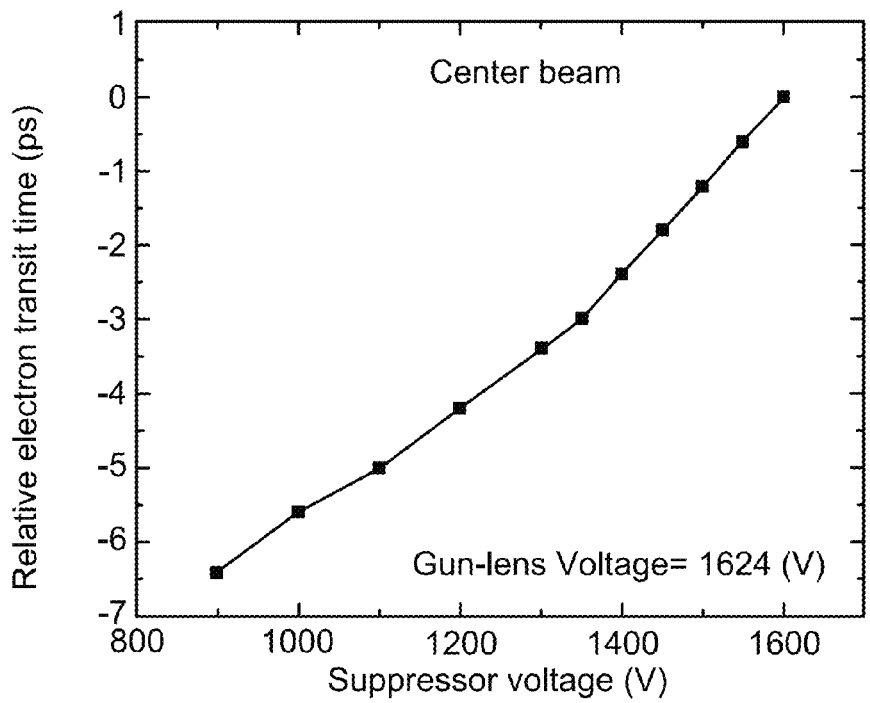
FIG. 12A is a plot illustrating relative electron transit time as a function of suppressor voltage for an electron beam from a center cathode according to an embodiment of the present invention.

FIG. 12A is a plot illustrating relative electron transit time as a function of suppressor voltage for an electron beam from a center cathode according to an embodiment of the present invention. Although providing a smaller range of variation in relative electron transit time, increases in suppressor voltage, measured at a fixed gun lens voltage of 1624 V, provided for an increase in relative electron transit time. As illustrated in FIG. 12A, for the center beam, an increase in the suppressor voltage of ~700 V resulted in an increase in the relative electron transit time of ~6 ps.

Figure 12B:
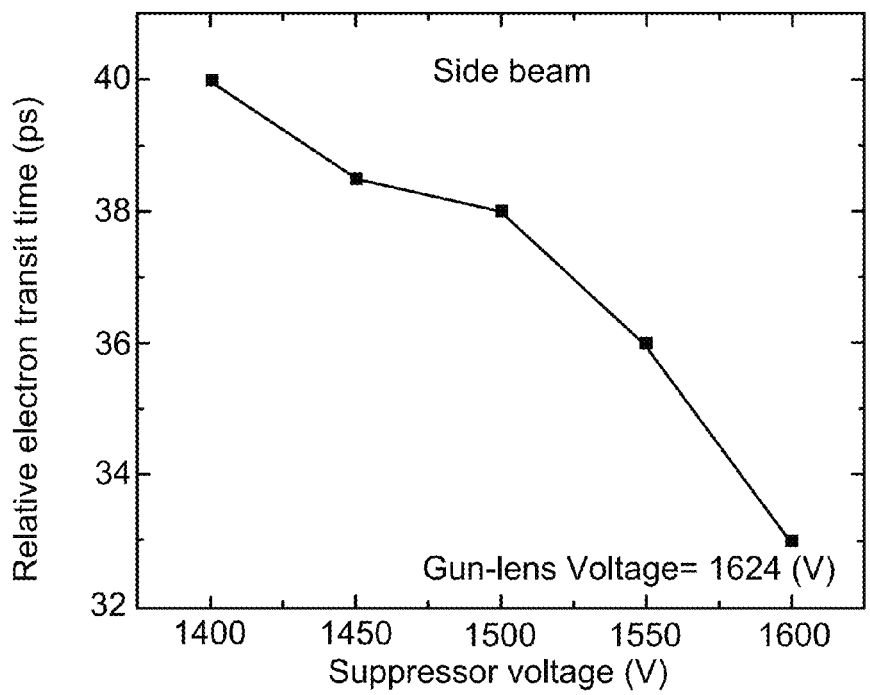
FIG. 12B is a plot illustrating relative electron transit time as a function of suppressor voltage for an electron beam from a side cathode according to an embodiment of the present invention.

FIG. 12B is a plot illustrating relative electron transit time as a function of suppressor voltage for an electron beam from a side cathode according to an embodiment of the present invention. Similar to the control of the center beam, the relative electron transit time for the side beam can be controlled over a range of about 7 ps by varying the suppressor voltage from ~1400 V to ~1600 V. As the suppressor voltage is increased, the relative electron transit time decreases.

Figure 13:
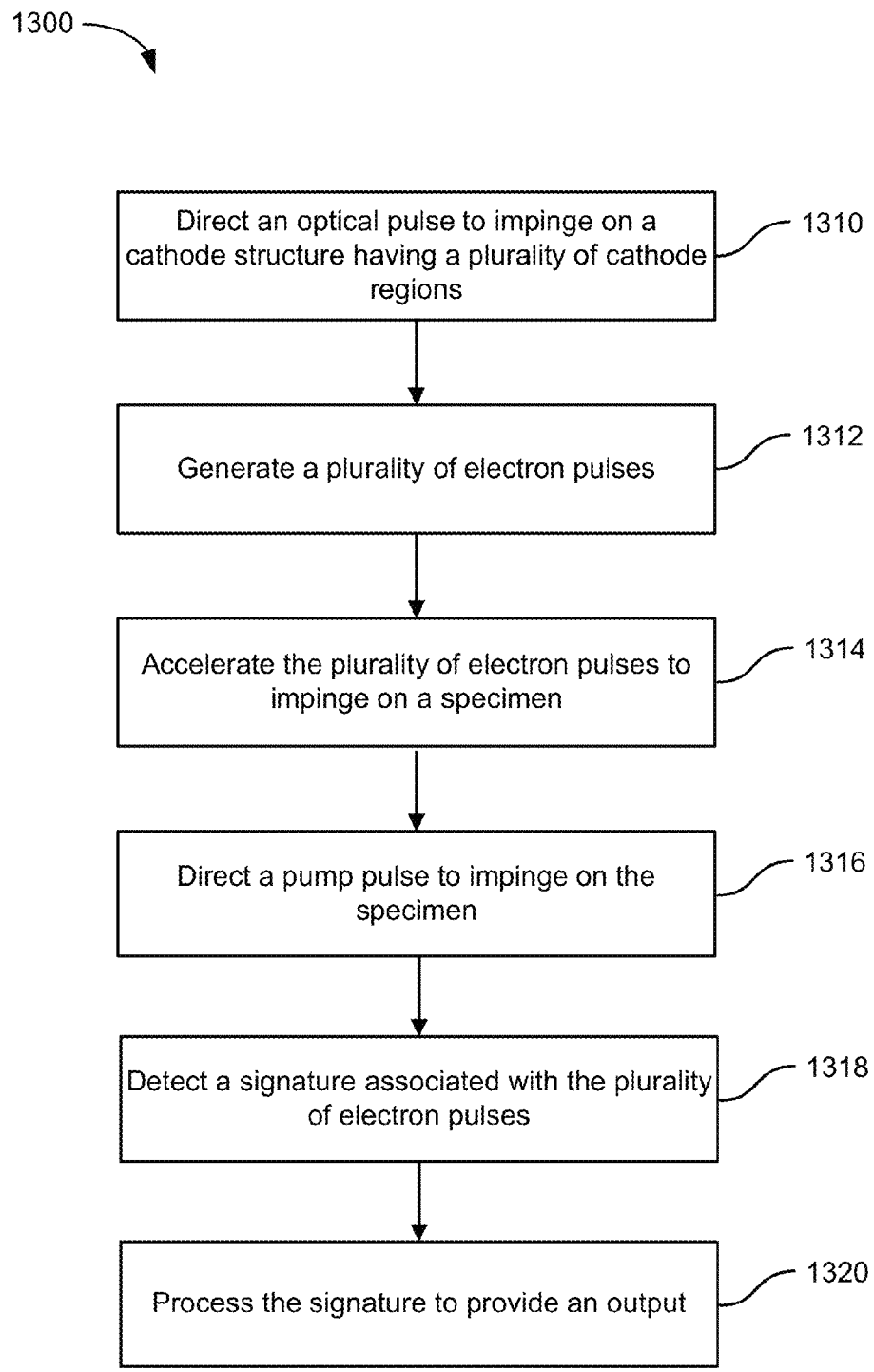
FIG. 13 is a simplified flowchart illustrating a method of operating an electron microscope according to an embodiment of the present invention.

FIG. 13 is a simplified flowchart illustrating a method of operating an electron microscope according to an embodiment of the present invention. The method 1300 includes directing an optical pulse to impinge on a cathode structure having a plurality of cathode regions (1310) and generating a plurality of electron pulses (1312). Each of the plurality of electron pulses is associated with one of the plurality of cathode regions. The method also includes accelerating the plurality of electron pulses to impinge on a specimen (1314) and directing a pump pulse to imping on the specimen (1316). In an embodiment, the optical pulse and the pump pulse originate from a single laser, with the optical pulse frequency converted into the ultraviolet region and the pump pulse frequency converted into the visible (e.g., green) region.

By controlling the microscope parameters during the acceleration process, the travel time of the plurality of electron pulses from the cathode structure to the specimen can be varied to introduce a time delay between the plurality of electron pulses as discussed in relation to FIGS. 11A-12B. As examples, control of the gun lens voltage and/or suppressor voltage can be used as some of the microscope parameters.

The method further includes detecting a signature associated with the plurality of electron pulses after the plurality of electron pulses have passed through the specimen (1318) and processing the signature to provide an output at an output device (1320). The signature can include one or more diffraction patterns. In an embodiment, each of the diffraction patterns are spatially separated from each other as a result of the spatial separation of the electron pulses at the cathode structure. In other embodiments, the signature can include an image associated with the plurality of electron pulses.

In some implementations, detecting the signature can include analyzing electron energy loss associated with the plurality of electrons in order to provide EELS analysis. In other implementations, detecting the signature can include energy filtering the plurality of electron pulses to provide a PINEM analysis.

It should be appreciated that the specific steps illustrated in FIG. 13 provide a particular method of operating an electron microscope according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 14:
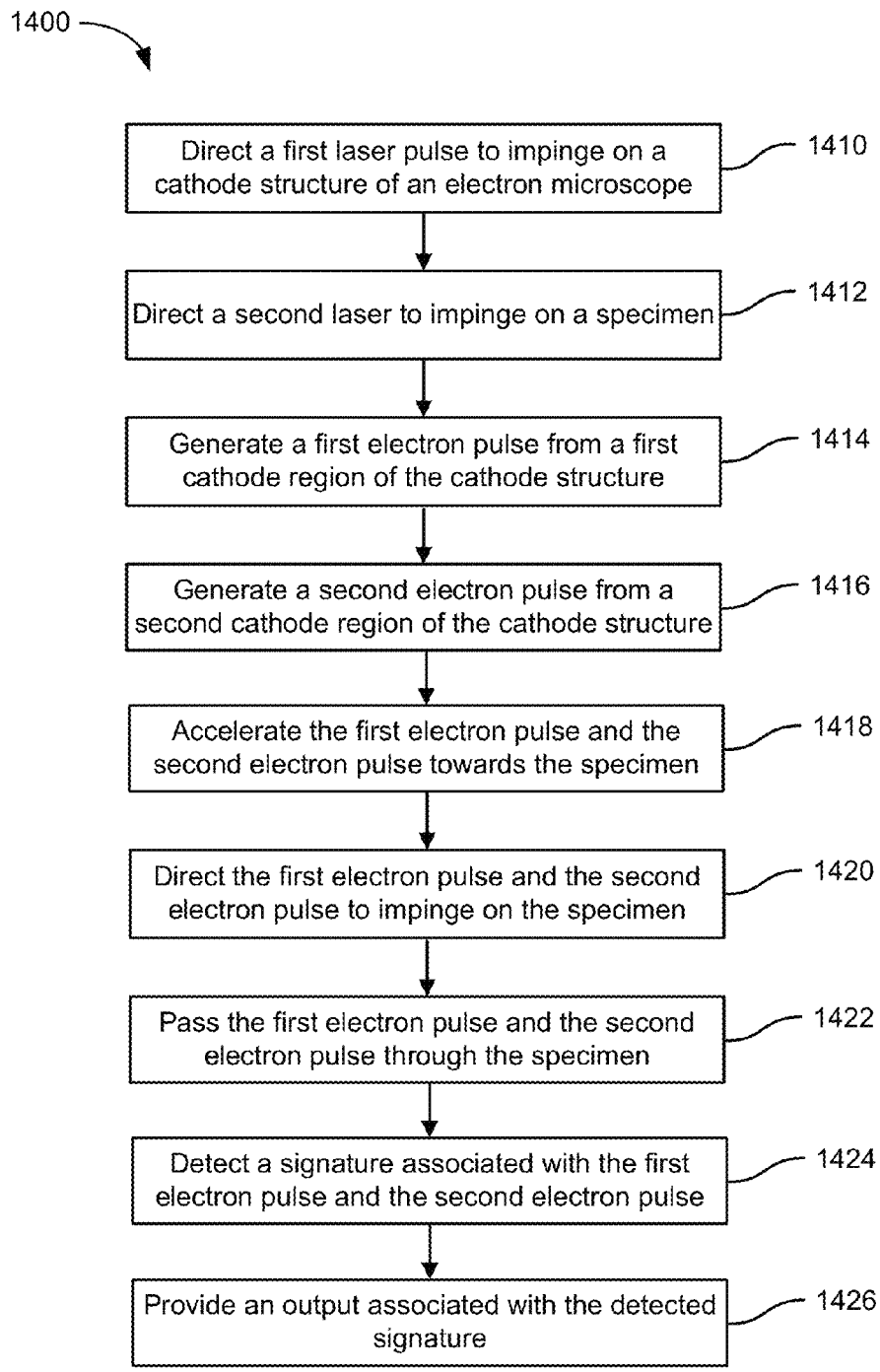
FIG. 14 is a simplified method of analyzing a specimen using an electron microscope according to an embodiment of the present invention.

FIG. 14 is a simplified method of analyzing a specimen using an electron microscope according to an embodiment of the present invention. The method 1400 includes directing a first laser pulse to impinge on a cathode structure of the electron microscope (1410) and directing a second laser pulse to impinge on the specimen (1412). The method also includes generating a first electron pulse from a first cathode region of the cathode structure in response to the first laser pulse (1414), generating a second electron pulse from a second cathode region of the cathode structure in response to the first laser pulse (1416), and accelerating the first electron pulse and the second electron pulse towards the specimen (1418). The first cathode region of the cathode structure and the second cathode region of the cathode structure can be spatially separated in the lateral direction, the longitudinal direction, or combinations thereof.

The method further includes directing the first electron pulse and the second electron pulse to impinge on the specimen (1420). The first electron pulse impinges on the specimen at a first time and the second electron pulse impinges on the specimen at a second time after the first time. During the acceleration of the first electron pulse and the second electron pulse, one or more microscope parameters may be controlled and varied to vary the time difference between the first time at which the first electron pulse impinges on the specimen and the second time at which the second electron pulse impinges on the specimen.

Additionally, the method includes passing the first electron pulse and the second electron pulse through the specimen (1422), detecting a signature associated with the first electron pulse and the second electron pulse (1424), and providing an output associated with the detected signature (1426). In an embodiment, the signature can include a first diffraction pattern associated with the first electron pulse and a second diffraction pattern associated with the second electron pulse. These diffraction patterns can be spatially separated from each other as a result of the spatial separation between the first cathode region and the second cathode region. In other embodiments, the signature includes an image.

It should be appreciated that the specific steps illustrated in FIG. 14 provide a particular method of analyzing a specimen using an electron microscope according to an embodiment of the present invention. Other sequences of steps may also be performed according to alternative embodiments. For example, alternative embodiments of the present invention may perform the steps outlined above in a different order. Moreover, the individual steps illustrated in FIG. 14 may include multiple sub-steps that may be performed in various sequences as appropriate to the individual step. Furthermore, additional steps may be added or removed depending on the particular applications. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:
1. An electron microscope system comprising:
a laser system operable to generate an optical pulse and a pump pulse; and
a microscope column including:
a multiple cathode structure having a plurality of spatially separated cathode regions, each of the cathode regions being operable to generate an electron pulse, wherein each of the electron pulses from each of the cathode regions impinge on a specimen at a different time;
an electron acceleration region adjacent the multiple cathode structure;
a specimen region operable to support the specimen; and
a detector.

2. The electron microscope system of claim 1 wherein the optical pulse comprises a femtosecond ultraviolet pulse and the pump pulse comprises a femtosecond green pulse.

3. The electron microscope system of claim 2 further comprising a first optical system operable to direct the femtosecond ultraviolet pulse to impinge on the multiple cathode structure and a second optical system operable to direct the femtosecond green pulse to impinge on the specimen.

4. The electron microscope system of claim 1 wherein the microscope column includes a suppressor in the electron acceleration region, wherein control electronics coupled to the suppressor are operable to vary electron transit time from the cathode region to the specimen.

5. The electron microscope system of claim 1 wherein the plurality of spatially separated cathode regions are operated at different voltages.

6. A method of operating an electron microscope, the method comprising:
directing an optical pulse to impinge on a cathode structure having a plurality of cathode regions;
generating a plurality of electron pulses, each of the plurality of electron pulses being associated with one of the plurality of cathode regions and impinging on a specimen at a different time;
accelerating the plurality of electron pulses to impinge on the specimen;
directing a pump pulse to imping on the specimen;
detecting a signature associated with the plurality of electron pulses after the plurality of electron pulses have passed through the specimen; and
processing the signature to provide an output at an output device.

7. The method of claim 6 wherein the signature comprises a diffraction pattern.

8. The method of claim 6 wherein the signature comprises an image associated with the plurality of electron pulses.

9. The method of claim 6 wherein detecting a signature comprises analyzing electron energy loss associated with the plurality of electrons.

10. The method of claim 6 further comprising detecting a signature comprises energy filtering the plurality of electron pulses.

11. The method of claim 6 wherein the optical pulse and the pump pulse originate from a single laser.

12. The method of claim 6 wherein accelerating the plurality of electron pulses comprises control of microscope parameters to vary a time delay between the plurality of electron pulses.

13. The method of claim 6 wherein the microscope parameters comprise at least one of gun lens voltage or suppressor voltage.

14. A method of analyzing a specimen using an electron microscope, the method comprising:
directing a first laser pulse to impinge on a cathode structure of the electron microscope;
directing a second laser pulse to impinge on the specimen;
generating a first electron pulse from a first cathode region of the cathode structure in response to the first laser pulse;
generating a second electron pulse from a second cathode region of the cathode structure in response to the first laser pulse;
accelerating the first electron pulse and the second electron pulse towards the specimen;
directing the first electron pulse and the second electron pulse to impinge on the specimen, wherein the first electron pulse impinges on the specimen at a first time and the second electron pulse impinges on the specimen at a second time after the first time;
passing the first electron pulse and the second electron pulse through the specimen;
detecting a signature associated with the first electron pulse and the second electron pulse; and
providing an output associated with the detected signature.

15. The method of claim 14 wherein the signature comprises a first diffraction pattern associated with the first electron pulse and a second diffraction pattern associated with the second electron pulse.

16. The method of claim 15 wherein the first diffraction pattern and the second diffraction pattern are spatially separated from each other.

17. The method of claim 14 wherein the signature comprises an image.

18. The method of claim 14 wherein accelerating the first electron pulse and the second electron pulse comprises modifying one or more microscope parameters to vary a time difference between the first time and the second time.

19. The method of claim 14 wherein the first cathode region of the cathode structure and the second cathode region of the cathode structure are spatially separated in both lateral and longitudinal directions.

* * * * *